(12) United States Patent
Shih et al.

(10) Patent No.: US 8,197,757 B2
(45) Date of Patent: Jun. 12, 2012

(54) ELECTRICAL INSULATION OF DEVICES WITH THIN LAYERS

(75) Inventors: Wan Y. Shih, Bryn Mawr, PA (US); Wei-Heng Shih, Bryn Mawr, PA (US); Joseph Capobianco, Marlton, NJ (US)

(73) Assignee: Drexel University, Philadelphia, PA (US)

(*) Notice: Subject to any disclaimer, the term of this patent is extended or adjusted under 35 U.S.C. 154(b) by 320 days.

(21) Appl. No.: 12/306,968

(22) PCT Filed: Jul. 6, 2007

(86) PCT No.: PCT/US2007/072940
§ 371 (c)(1),
(2), (4) Date: Dec. 30, 2008

(87) PCT Pub. No.: WO2008/006060
PCT Pub. Date: Jan. 10, 2008

(65) Prior Publication Data
US 2010/0068490 A1 Mar. 18, 2010

Related U.S. Application Data

(60) Provisional application No. 60/806,765, filed on Jul. 7, 2006.

(51) Int. Cl.
*B01L 99/00* (2010.01)
*B32B 9/04* (2006.01)

(52) U.S. Cl. ....... 422/69; 422/82.13; 436/501; 436/518; 438/49; 428/447; 428/450; 428/702

(58) Field of Classification Search .......................... None
See application file for complete search history.

(56) References Cited

U.S. PATENT DOCUMENTS

| | | | |
|---|---|---|---|
| 5,182,143 A * | 1/1993 | Holmes-Farley et al. | 427/409 |
| 6,270,846 B1 * | 8/2001 | Brinker et al. | 428/64.1 |
| 6,451,436 B1 * | 9/2002 | Komatsu et al. | 428/447 |
| 6,458,327 B1 | 10/2002 | Vossmeyer et al. | |
| 6,465,368 B2 | 10/2002 | Inoue et al. | |
| 6,495,264 B2 * | 12/2002 | Hayashi et al. | 428/447 |
| 6,787,191 B2 * | 9/2004 | Hanahata et al. | 427/387 |
| 7,345,351 B2 * | 3/2008 | Moon et al. | 257/499 |
| 2002/0155303 A1 | 10/2002 | Wielstra et al. | |
| 2004/0022677 A1 | 2/2004 | Wohlstadter et al. | |
| 2004/0038040 A1 * | 2/2004 | Schumann et al. | 428/423.1 |
| 2004/0202874 A1 * | 10/2004 | Iwabuchi et al. | 428/447 |
| 2005/0112386 A1 * | 5/2005 | Akiyama et al. | 428/447 |
| 2007/0298267 A1 * | 12/2007 | Zhong et al. | 428/447 |
| 2008/0035494 A1 * | 2/2008 | Gomez et al. | 205/792 |
| 2009/0297832 A1 * | 12/2009 | Hatta et al. | 428/328 |

FOREIGN PATENT DOCUMENTS

| | | | |
|---|---|---|---|
| WO | 2004061991 A1 | | 7/2004 |
| WO | WO 2005/118503 | * | 12/2005 |
| WO | WO 2008/086465 | * | 7/2008 |

OTHER PUBLICATIONS

"Self-Assembled Silica Gel Networks" authored by Wang et al., and published in JACS (1998) 102, 5852-5853.*
Formation and Structure of Self-Assembled Monolayers authored by Ulman and published in Chemical Reviews (1996) 96, 1533-1554.*
abstract for WO 2008/086465.*
Brito, et al., "Absorption of 3-Mercaptopropyltrimethoxysilane and 3-Aminopropyltrimethoxysilane at Platinum Electrodes", Journal of Electroanalytical Chemistry 520, 2002, pp. 47-52.
Niedziolka, et al., "Characterisation of Gold Electrodes Modified with Methyltrimethoxysilane and (3-Mercaptopropyl) Trimethoxysilane sol-gel Processed Films", Journal of Electroanalytical Chemistry, 578, 2005, pp. 239-245.
Katiyar, et al., "Electrical Properties of Amorphous Aluminum Oxide Thin Films", Acta Materialia, 53, 2005, pp. 2617-2622.
Chen, et al., "Electrochemical and Spectroscopic Characcterization of Surface Sol-Gel Processes", Langmuir, 2004, 20, pp. 8762-8767.
Feili, et al., "Encapsulation of Organic Filed Effect Transistors for Flexible Biomedical Microimplants", Sensors and Actuators A, 120, 2005, pp. 101-109.
Thompson, et al., "Hydrolysis and Condensation of Self-Assembled Monolayers of (3-Mercaptopropyl) Trimethoxysilane on Ag and Au Surfaces", Langmuir, 1997, 13, pp. 2291-2302.
Hwang, et al., "In-Situ Quantitative Analysis of a Prostate-Specific Antigen (PSA) Using a Nanomechanical PZT Cantilever", Miniaturisation for Chemistry, Biology & Bioengineering, Lab Chip, pp. 547-552, 4, 2004.
Bondoux, et al., "MgO Insulating Films Prepared by Soul-Gel Route for SiC Substrate", Journal of European Ceramic Society, 25, 2005, pp. 2795-2798.
Ohnmacht, et al., "Microcoils and Microrelays—An Optimized Multilayer Fabrication Process", Sensors and Actuators, 83, 2000, pp. 124-129.
Cho, et al., "Micro-Scale Metallization on Flexible Polyimide Substrate by Cu Electroplating Using SU-8 Photoresist Mask", Thin Solid Films 475, 2005, pp. 68-71.
Che, et al., "Molecular Recognition based on (3-mercaptopropyl) Trimethoxysilane Modified Gold Electrodes", Journal of Electroanalytical Chemistry, 417, 1996, pp. 155-161.
Khabari, et al., "Partially Ionized Beam Deposition of Parylene", Journal of Non-Crystalline Solids, 351, 2005, pp. 3536-3541.
Tslonsky, et al., "Sol-Gel-Derived Ceramic-Carbon Composite Electrodes: Introduction and Scope of Applications", Anal. Chem., 66, 1994, pp. 1747-1753.
Nguyen, et al., "Synthesis and Characterization of a Photosensitive Polyimide Precursor and its Photocuring Behavior for Lithography Applications", Optical Materials, 29, 2007, pp. 610-618.

(Continued)

*Primary Examiner* — Marc Zimmer
(74) *Attorney, Agent, or Firm* — Knoble Yoshida & Dunleavy, LLC

(57) ABSTRACT

A novel, economical electrical insulation method for the production of ultra-thin insulation layers using a solution coating method. Thin hydrophobic self-assembled bi-functional layers of less than 10 nm thick were deposited by a simple solution method and demonstrated to electrically insulate micro-/nano-devices for in-water detection applications. The insulation layer includes a hydrophobic group which repels water and permits superb insulation properties of the ultra-thin layers. The insulation layer has the additional advantages that it binds to a metal or metal oxide surface and to sensing receptors by covalent bonding using standard silane chemistry.

19 Claims, 9 Drawing Sheets

OTHER PUBLICATIONS

Capobianco, et al., "3-Mercaptopropyltrimethoxysilane as Insulating Coating and Surface for Protein Immobilization for Piezoelectric Microcantilever Sensor", Review of Scientific Instruments, 78, 2007, 3 pages.

Capobianco, et al. "Methyltrimethoxysilane-Insulated Piezoelectric Microcantilevers for Direct, All-Electrical Biodetection in Buffered Aqueous Solutions", Review of Scientific Instruments, 77, 2006, 6 pages.

* cited by examiner

ELECTRICAL INSULATION OF DEVICES WITH THIN LAYERS

STATEMENT OF GOVERNMENT INTEREST

This invention was reduced to practice with Government support under Grant No. R01 EB000720 awarded by the National Institutes of Health; the Government is therefore entitled to certain rights in the invention.

BACKGROUND OF THE INVENTION

1. Field of the Invention

The present invention relates to micro-scale and nano-scale devices. More particularly, the present invention relates to electrical insulation of micro-scale and nano-scale devices for use in aqueous environments.

2. Description of the Related Technology

Due to the small size of micro- and nano-devices, the insulation layer must be very thin, and yet effective for electrical insulation so as not to adversely affect the mechanical performance of the micro-/nano-devices. In addition, the method for providing the insulation layer on the devices must also be economical for large scale industrial applications.

In biosensing applications, the micro-/nano-devices must be electrically insulated in a manner that allows them to be completely submerged in aqueous ionic buffers without a short circuit. In addition, the insulation layer must be able to accommodate immobilization of a receptor on the insulation layer and exhibit good bonding with the electrode surface, as well as with the immobilized receptor.

Thin ceramic layers such as MgO (C. Bondoux, P. Prené, P. Belleville, F. Guillet, S. Lambert, B. Minot and R. Jérisian, "MgO Insulating Films Prepared by Sol-gel Route for SiC Substrate," *J Europ. Ceram, Soc.*, 25(12), 2795-2798 (2005)); as well as $Al_2O_3$, $Si_3N_4$, $Ta_2O_5$, $TiO_2$, $BaTiO_3$ and $SrTiO_3$ (P. Katiyar, C. Jin and R. J. Narayan, "Electrical Properties of Amorphous Aluminum Oxide Thin Films," *Acta Materialia*, 53(9), 2617-2622, (2005) and the references cited therein) (Nguyen, L. T. T. et al., cited infra) have been shown to be effective insulation layers, but they require high-vacuum chemical vapor deposition (CVD) for applications. CVD is expensive and slow. Although polymeric insulation coatings such as polyimides (L. T. T. Nguyen, H. N. Nguyen and T. H. T. La, "Synthesis and Characterization of a Photosensitive Polyimide Precursor and its Photocuring Behavior for Lithography Applications," *Optical Materials*, In Press, Corrected Proof, Available online 3 Jan. 2006, (http://www.sciencedirect.com/science/article/B6TXP-4HYD9 KB-3/2/bb4da50c417e914af8950e8ba0ceb1b3 and S. H. Cho, S. H. Kim, N.-E. Lee, H. M. Kim and Y. W. Nam, "Micro-Scale Metallization on Flexible Polyimide Substrate by Cu Electroplating Using SU-8 Photoresist Mask," *Thin Solid Films*, 475, 1-2, Proceedings of the 4th Asian-European International Conference on Plasma Surface Engineering, 22 Mar. 2005, Pages 68-71. (http://www.sciencedirect.com/science/article/B6TW0-4DTKFCN 5/2/100c045e03c50e9a3aee 6120537ded2a), and benzocyclobutene (BCB) (M. Ohnmacht, V. Seidemann and S. Buttgenbach, "Microcoils and Microrelays: an Optimized Multilayer Fabrication Process," *Sensors and Actuators*, 83, 124-129 (2000)), can be deposited using a wet solution method, they require a thickness of tens of microns to be effective, too thick for micro-/nano-device applications. Thinner polymeric layers, such as parylene, require use of CVD for applications (D. Feili, M. Schuettler, T. Doerge, S. Kammer, and T. Stieglitz, "Encapsulation of Organic Field Effect Transistors for Flexible Biomedical Microimplants," *Sensors and Actuators, A*, 120, 101-109 (2005) and K. S. Hwang, J. H. Lee, J. Park, D. S. Yoon, J. H. Park and T. S. Kim, "In-situ Quantitative Analysis of a Prostate-Specific Antigen (PSA) Using a Nanomechanical PZT Cantilever," *Lab Chip* 4, 547 (2004)). Additional disadvantages of parylene include poor adhesion to the electrode surface (A. Khabari and F. K. Urban III, "Partially Ionized Beam Deposition of Parylene," *J. Non-Crystalline Solids*, 351, 3536-3541 (2005)) and difficulties in the subsequent step of receptor immobilization (Feili, D. et al., cited infra).

In summary, the disadvantages of the current insulation methods include:

(1) Requiring high-vacuum physical or chemical vapor deposition, which is expensive and slow,
(2) Requiring a thicker layer than the thickness of the insulation layers achieved by the present invention,
(3) Lacking the ability to covalently bond to the electrode surface, and/or
(4) Lacking the ability to covalently bond to provide an immobilized antibody/receptor.

Recently, a patent application was for a piezoelectric biosensor which can perform rapid, direct, and in situ detection of various molecular species in liquid (W. Y. Shih, W.-H. Shih, and Z. Shen, "Piezoelectric Cantilever Sensor," Patent Application No. PCT/US2004/036705, Oct. 27, 2004).

Accordingly, there is a need in the art for improved insulation layers for use in electromechanical devices.

SUMMARY OF THE INVENTION

The present invention provides a very thin insulation layer which lends itself to bonding of a receptor thereon. More specifically, micro-/nano-devices are electrically insulated with bi-functional thin layers using a solution method. The present invention may be applied to various examples of piezoelectric biosensors such as lead magnesium niobate-lead titanate (PMN-PT)/metal and lead zirconate titanate (PZT)/glass piezoelectric microcantilever sensor (PEMS).

The insulation method utilizes a bi-functional molecule that has a hydrophobic group and a silanol group that allows the bi-functional molecule to covalently bond to a material including a receptor.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENTS

Figure 1:
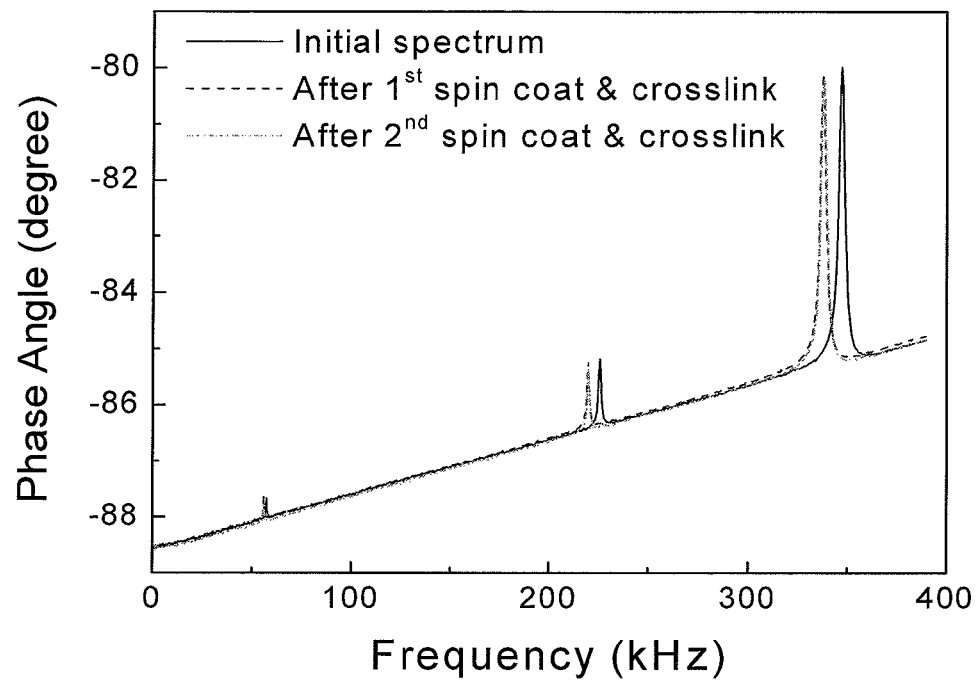
FIG. 1 shows the resonance spectrum of the initial PMN-PT/Sn PEMS (solid line), the PMN-PT/Sn PEMS after one layer of methyltrimethoxysilane (MTMS) coating was applied (dashed line), and after a second MTMS coating was applied (dash-dot-dot line).

One objective of the present invention is to electrically insulate micro- and nano-devices, including micro-electromechanical systems (MEMS) and nano-electromechanical systems (NEMS) for use in applications in aqueous environments. This is accomplished by electrically insulating micro-/nano-devices with bi-functional thin layers using a solution method.

The insulation method utilizes a bi-functional molecule that has a hydrophobic group, for example, alkyl, sulfhydryl, phenyl, etc., on one end and silanol groups on the other end that allow the molecule to covalently bond to any material that can perform silane chemistry.

A general structure of a silane-based bi-functional molecule is:

$$(RO)_3Si(CH_2)_y-X \quad (I)$$

wherein y is an integer from 1-20, and the central silicon atom is bonded to three hydrolysable silanol groups (RO) on one end and the molecule includes an organo-functional group (X) on the other end.

The silanols can react with other silanols to form a covalent siloxane bond (—Si—O—Si—) on a glass surface, or with metal hydroxyl groups on minerals or metals to form a stable —Si—O-M bond, where M represents the metal.

The organo-functional group (X) can be activated and made reactive toward organic species. For the present electrical insulation application, the organo-functional group can be any hydrophobic group such as alkyl, sulfhydryl, phenyl, etc. The hydrophobic group prevents water from contacting the electrode surface, thus enabling electrical insulation in water with an ultra thin insulation layer, which may be no thicker than a few nanometers. For example, the present invention enables insulation layers of less than 10 nm in thickness. Insulation layers in accordance with the present invention are generally at least 1 nm in thickness.

In addition, the silanol group can covalently bond to an electrode surface, providing excellent bonding between the electrode surface including a receptor, and the insulation layer. Typically, CVD-based techniques can not provide good bonding with an electrode surface.

In one embodiment, a minimum of two silanol groups is required: one for the bonding to the silanol or hydroxyl group of the base layer and the other for bonding to the silanol or hydroxyl group of the next bi-functional layer that may be for further insulation or be a receptor useful, for example, for protein/DNA coupling.

In order to covalently link the silanol to the surface, hydroxyl or silanol groups on the metal surface are necessary. Hydroxyl groups are abundant on most metal oxides, polymeric surfaces, and glass surfaces. The insulation method of the present invention can thus be applied to surfaces that can be converted to contain hydroxyls or silanols.

The bi-functional molecule used for insulation or a different bi-functional molecule containing silanes may be used to couple proteins (or small peptide chains) and DNA to the insulation layer surface. Coupling can also be accomplished in accordance with the present invention by the use of any molecule or macromolecule containing the functional groups necessary for the formation of a covalent bond.

The protein/DNA coupling bi-functional molecule can have at least one silanol group (methoxy, ethoxy, etc.) to covalently bind to the insulation layer and one residual group (hydroxyl, thiol, amine, amide, carboxylic acid, aldehyde, ketone anhydride halide, alkene, alkyne, etc) that can be used for protein/DNA conjugation in conjunction with another bi-functional linker to covalently couple to proteins or small peptide chains, DNA, and various other macromolecules. Many kits that can be used for this purpose are commercially available.

In addition to varying the residual group, one can also vary the number of carbon atoms in between the residual group and the silicon atom.

Methyltrimethoxysilane (MTMS) and 3-mercaptopropyl-trimethoxysilane (MPS) are examples of useful bi-functional molecules. These molecules can covalently bond to electrode surfaces such as Ni, Sn, Ti, or Cr that have a natural oxide layer on the surface using standard silane chemistry. These molecules can also covalently bond to a noble metal surface such as gold and platinum using MPS as a bonding layer. The thiol group of the MPS bonding layer forms a covalent bond with the noble metal surface. The silanols of the MPS bonding layer form a covalent bond with the silanols of the insulating MTMS or MPS layer using conventional silane chemistry.

The surface of the MTMS or MPS layer has plenty of silanol groups. In theory, about one fourth of the MTMS or MPS surface is occupied by the methyl (thiol) groups and three fourths of the MTMS or MPS surface is occupied by silanol groups. The silanol groups on the insulation layer surface will allow easy covalent immobilization of receptors necessary for detection applications.

The present invention employs the hydrophobicity of the hydrophobic group to repel water, thus allowing the fabrication of functional electrical insulation layers of less than 2000 nm, more preferably, less than 10 nm in thickness. The silane/silanol groups may be used for covalent coupling to the electrode surface as well as the antibody/receptor.

The present invention can be applied to electrodes with a natural oxide surface, such as Ti, Ni, Sn, and Cr, and can also be used on metals without a surface oxide, such as Au and Pt, via a bi-functional linker such as MPS. Unlike known thin insulation coatings which require high vacuum chemical vapor deposition for application, the insulation layer of the present invention can be deposited using a solution coating method, such as spin coating, which renders the method suitable for use in large-scale industrial production processes.

The present invention is useful for electrical insulation of devices for application in aqueous environments. The present invention is applicable to electromechanical devices in general, and, more specifically, is particularly useful for microelectromechanical systems (MEMS) and nano-electromechanical systems (NEMS).

The present invention also encompasses micro-electromechanical systems (MEMS) and nano-electromechanical systems (NEMS) which comprise the insulation layer of the invention, as well as biosensors such as piezoelectric cantilevers, as well as other types of cantilever sensors including the insulation layer of the invention. These sensors can have receptors for a variety of different reactive species, such as antibodies, covalently bonded to the insulation layer.

EXAMPLE 1

In this example, lead magnesium niobate-lead titanate (PMN-PT)/Sn piezoelectric microcantilever sensors (PEMS) were used to illustrate one embodiment of the present invention. PMN-PT/Sn PEMS were constructed from freestanding PMN-PT films[18,19] of 22 μm in thickness. A 30-nm thick nickel layer with a 15-30 nm thick chromium bonding layer was deposited on one side of the PMN-PT freestanding film by sputtering. A 4-μm thick tin layer was electroplated on the nickel surface to form the non-piezoelectric layer. A 150-nm thick platinum layer with a 10-nm thick titanium layer was evaporation coated on the other face of the film as the other electrode. The PMN-PT/Sn bilayer was then embedded in wax and cut to the cantilever shape with a wire saw (Princeton Scientific Precision, Princeton, N.J.). After attaching the wires to the top and bottom electrodes using conductive glue, the PMN-PT/Sn strips were then glued to a glass substrate to form the microcantilevers.

To insulate the tin electrode of a PMN-PT/Sn PEMS, the PEMS was first soaked in a diluted (1:40 in water) piranha solution (two parts of 98% sulfuric acid (Fisher, Fair Lawn, N.J.) with one part of 30% hydrogen peroxide (Fisher Biotech, Fair Lawn, N.J.) at 20° C. for 2 min to clean and oxidize the tin surface. The oxidized tin surface was then coated with three methyltrimethoxysilane (MTMS) (95% Aldrich, Milwaukee, Wis.) coatings for insulation. During each coating step, the tin side of the PEMS was covered with MTMS for 1 minute followed by spinning at 2500 RPM for 30 seconds (Photoresist Spinner, Headway Research Inc). The PEMS was then soaked in de-ionized water overnight for cross-linking, followed by spinning at 2500 RPM for 30 sec and overnight vacuum-oven (Model 1400E, VWR International) drying at 762 mm Hg. This MTMS coating procedure was repeated one more time before the PEMS was used for detection in an aqueous environment.

To demonstrate bio-detection in an aqueous environment, antibodies were immobilized on the platinum surface of the PEMS. For antibody immobilization, the PEMS was first cleaned with a diluted (1:40 in water) piranha solution. After rinsing with de-ionized water, the PEMS was then submerged in a 2-mM aqueous solution of 3-mercaptopropionic acid (MPA) (99+% Aldrich, St. Louis Mo.) for 3 hours in order for the sulfhydryl group of the MPA to attach to the platinum surface (D. B. Colin, E. B. Troughton, Y. T. Tao, J. Erall, M. W. George and G. N. Ralph, "Formation of Monolayer Films by the Spontaneous Assembly of Organic Thiols From Solution onto Gold," *J. Am. Chem. Soc.* 111, 321-325 (1989); M. Hasan, D. Bethell and M. Brust, "The Fate of Sulfur-Bound Hydrogen on Formation of Self-Assembled Thiol Monolayers on Gold: $^1$H NMR Spectroscopic Evidence from Solutions of Gold Clusters," *J. Am. Chem. Soc.*, 124, 1132-1133 (2002); and C. Gutierrez-Wing, J. A. Ascencio, M. Pérez-Alvarez, M. Marin-Almazo, and M. Jose-Yacaman, "On the Structure and Formation of Self-Assembled Lattices of Gold Nanoparticles," *Journal of Cluster Science*, 9(4), (1998)). The carboxyl group of the immobilized MPA was then activated using a 5 mg/ml aqueous solution of N-Hydroxysuccinimide (NHS) (98% Aldrich, St. Louis, Mo.) and 1-Ethyl-3-(3-dimethylaminopropyl)-carbodiimide (EDC) (Sigma, St. Louis, Mo.) for 30 minutes to be reactive to primary amines (lysine) in the antibody (Z. Grabarek and J. Gergely, "Zero-length Crosslinking Procedure with the use of Active Esters," *Analytical Biochemistry*, 185(1) 131-135 (1990); D. G. Hoare, D. E. Koshland, Jr, "A Method for the Quantitative Modification and Estimation of Carboxylic Acid Groups in Proteins," *J Biological Chem.*, 242(10) 2447-2453 (1967); and L. A. Lyon, M. D. Musick, P. C. Smith, B. D. Reiss, D. J. Peña and M. J. Natan, "Surface Plasmon Resonance of Colloidal Au-modified Gold Films," *Sensors and Actuators B*, 54(1-2), 118-124 (1999)). Finally, the PEMS was dipped in a 400 nM anti-*E. coli* antibody (Kirkegaard & Perry Laboratory, Gaithersburg, Md.) in a phosphate buffered saline (PBS) solution (Sigma, St. Louis, Mo.). The heat deactivated *E. coli* was obtained from Kirkegaard & Perry Laboratory at Gaithersburg, Md.

The PEMS had a 22 μm thick PMN-PT layer as the piezoelectric layer and an 8-μm thick tin layer as the non-piezoelectric layer and was 650 μm in length and 900 μm in width. The initial resonance spectrum of a PMN-PT/tin micro-cantilever measured in air with an electrical impedance analyzer (Agilent 4294A, Agilent, Palo Alto, Calif.) before insulation is shown as the solid line in FIG. 1. The initial resonance spectrum of the PMN-PT/tin micro-cantilever exhibited three peaks at 57, 226, and 347 kHz, respectively. The first, second, and third resonance peak exhibited quality factors, Q, of about 100, 130, and 100, respectively. Q is defined as the ratio of the resonance frequency to the width of the resonance peak at half the peak height.

The resonance spectra of the same cantilever in air after the first and second MTMS spin coating steps, and following cross-linking, are shown in FIG. 1 as the dashed line and dash-dot-dot line, respectively. The MTMS coatings did not affect the in-air resonance peak height or peak width and the in-air Q values of all three resonance peaks remained close to their pre-coating values, within an error of about 5 Hz.

A 5-MHz quartz crystal microbalance (QCM) (Stanford Research Systems, Sunnyvale, Calif.) was used to quantify the thickness of each MTMS coating layer. The gold electrode of the QCM was first cleaned with a piranha solution for 30 minutes, followed by rinsing with de-ionized water and ethanol. The QCM was then soaked in a 40-mM solution of mercaptopropyltrimethoxysilane (MPS) (97% Alfa Aesar, Ward Hill, Mass.) in ethanol for 3 hours and rinsed with ethanol. The QCM was then immediately soaked in 0.01 M NaOH (99.99% Aldrich, Milwaukee, Wis.) for 48 hours to facilitate cross linking. This procedure produced silanol groups on the QCM surface to mimic the hydroxyl groups that existed on the naturally oxidized tin surface. The QCM was subsequently rinsed with de-ionized water.

Upon completion of the process, the resonance frequency was recorded using an impedance analyzer. The results are shown in Table I.

(dotted line). As can be seen from FIG. 3, the cantilever retained two resonance peaks in PBS although both the resonance peak intensities and peak frequencies were lowered as a result of both the effect of viscous damping and the mass of the liquid that moved with the cantilever (W. Y. Shih, X. Li, H. Gu, W.-H. Shih, and I. A. Aksay, "Simultaneous Liquid Viscosity and Density Determination Using Piezoelectric Unimorph Cantilevers," *J. Appl. Phys.*, 89, 1497 (2001)). Comparing the spectrum in PBS and that in air, the first resonance peak disappeared in PBS, the second peak shifted from 226 kHz in air with Q=127 to 187 kHz with Q=65, and the third peak shifted from 347 kHz with Q=95 to 263 kHz with a Q=43, indicating that the MTMS coatings electrically insulated the PMN-PT/tin micro-cantilever and maintained a good Q value.

Figures 4A, 4B:
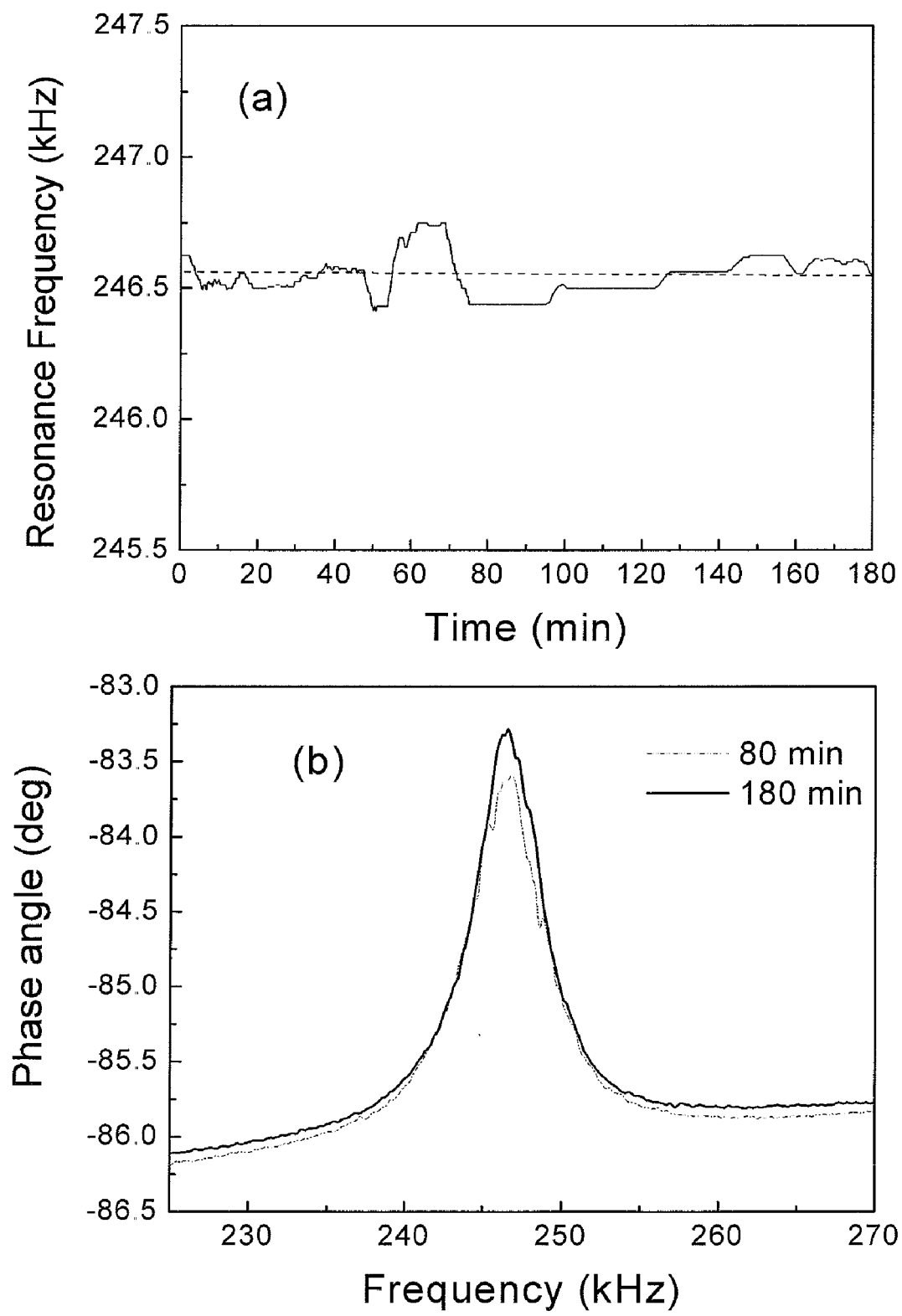
FIG. 4a shows the resonance frequency versus time of the cantilever sensor of Example 1.
FIG. 4b shows the resonance spectrum at t=80 min and t=180 min of the MTMS-insulated PMN-PT/Sn PEMS of Example 1 in a phosphate buffer saline solution (PBS).

The stability of MTMS coating in PBS is shown in FIGS. 4a and 4b. FIG. 4a shows the resonance frequency of the third peak of a MTMS-coated cantilever in PBS versus time and FIG. 4b the resonance spectra of the cantilever shown in FIG. 4a at t=80 min (dashed-dotted line) and 180 min (solid line). As can be seen from FIG. 4a, the resonance frequency remained stable with a standard deviation of about 75 Hz for the three hours when the cantilever was monitored. The spectra shown in FIG. 4b indicated that the resonance peak height

TABLE I

Resonance frequency shifts and thickness of MTMS coatings on 5 MHz QCM

| | Initial frequency (Hz) | frequency after 1st coat (Hz) | 1st-coat Δf (Hz) | 1st-coat thickness (nm) | frequency after 2nd-coat (Hz) | 2nd-coat Δf (Hz) | 2nd-coat thickness (nm) | Total coating thickness (nm) |
|---|---|---|---|---|---|---|---|---|
| QCM #1 | 5005395 | 50053305 | −65 | 3.9 | 5005277 | −53 | 3.2 | 7.1 |
| QCM #2 | 4994955 | 49948650 | −90 | 5.4 | 4994796 | −69 | 4.1 | 9.5 |
| QCM #3 | 5000965 | 50009020 | −63 | 3.8 | 5000845 | −57 | 3.4 | 7.2 |
| QCM #4 | 4991240 | 49910850 | −155 | 9.3 | 4991056 | −29 | 1.8 | 11 |
| Average | | | −9.3 | 5.6 | | −52 | 3.1 | 8.7 |

After the MPS coating, MTMS was coated on the MPS modified QCM surface. The resonance frequency after each coating was recorded and listed in Table I. From the resonance frequency shifts, $\Delta f_{QCM}$, the MTMS coating thickness was calculated using the following equation, $$\Delta t = -\frac{2f^2}{\sqrt{\mu_q/\rho_q}} \Delta f_{QCM}. \quad \text{(II)}$$

where f=5 MHz was the natural resonance frequency of the QCM, $\mu_q$=2.947×10$^{11}$ dyne/cm$^2$ and $\rho$=2.648 g/cm$^3$, the shear modulus and density of the QCM, respectively (Z. Lin, C. M. Yip, I. S. Josheph, and M. D. Ward, *Anal. Chem.*, 65, 1546-51 (1993)).

Figure 2:
FIG. 2 shows a water droplet on an MTMS-coated surface. The high contact angle indicates the hydrophobicity of the methyl groups on the MTMS surface.

As can be seen from Table I, with four QCM measurements, the average thickness of the first and second MTMS coatings were 5.6 and 3.1 nm, respectively. The wetting angle of a water droplet on the hydrophilic MPS-modified QCM surface before the MTMS coatings was 37°. After two coatings of MTMS, the surface became hydrophobic (see FIG. 2) and the wetting angle became 69°.

Figure 3:
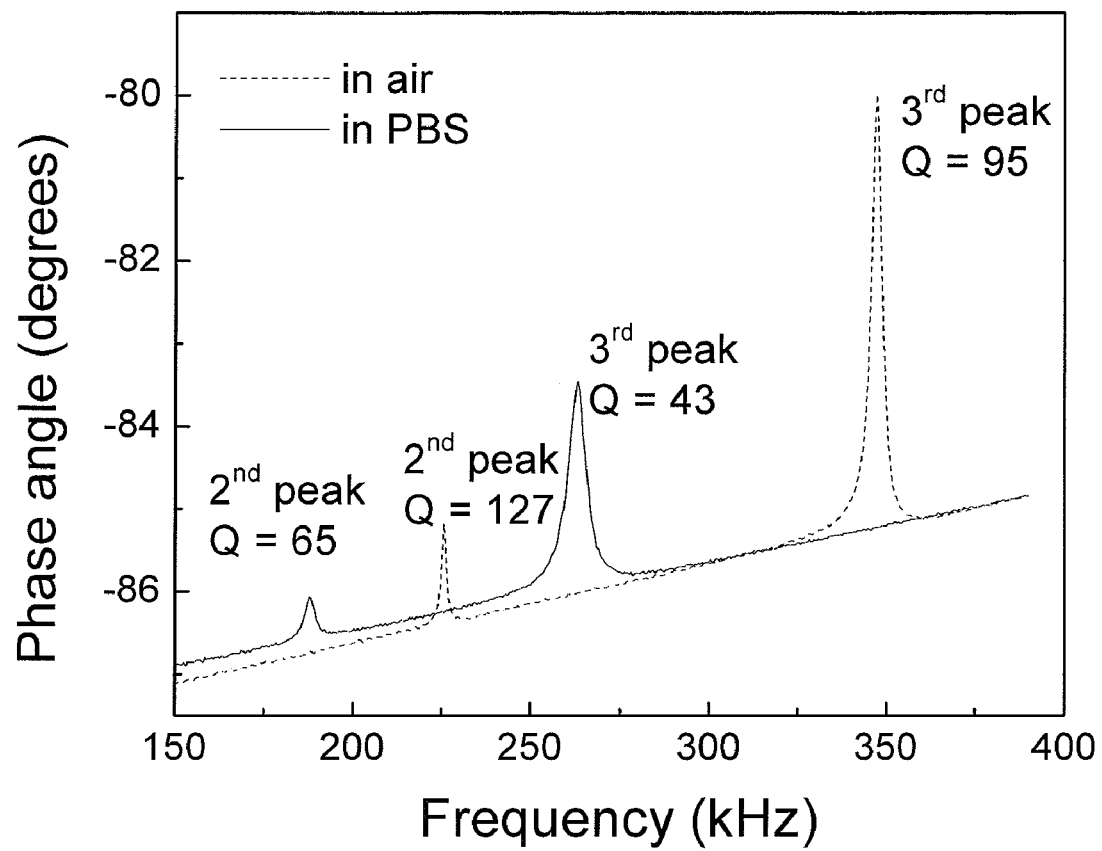
FIG. 3 shows the resonance frequency spectrum of the MTMS-insulated PMN-PT/Sn PEMS in air (dashed line) and in a phosphate buffer saline solution (PBS) (solid line).

After MTMS coating, the cantilever was then submerged in a phosphate buffer solution (PBS) (Sigma, St. Louis, Mo.). The resonance spectrum of the MTMS coated cantilever in PBS is shown in FIG. 3 as the solid line. Also shown is the spectrum of the same MTMS-coated cantilever taken in air was also stable. These results indicated that the MTMS coated cantilever can be used for detection in PBS as long as the detected frequency shift was larger than the standard deviation. As can be seen, both the resonance frequency and resonance peak shape of the MTMS-insulated PMN-PT/Sn PEMS were stable over time, indicating that the thin MTMS coating layer can indeed provide the necessary electrical insulation of the PEMS in-water detection applications.

*E. coli* Detection

For *E. coli* detection, the antibody-immobilized cantilever was immersed in a home-built flow cell (J.-P. McGovern, W. Y. Shih, and W.-H. Shih, "Direct Detection of *Bacillus Anthraces* Spores," to be submitted to *Anal. Chem.*) with a peristaltic pump (model 77120-62, Cole-Parmer Master Flex, Vernon Hills Ill.). The flow cell contained 1 ml of *E. coli* suspension. The detection was carried out with the cantilever's two faces tangential to the flow at a flow rate of 0.5 ml/min for 30 min. After each detection, the *E. coli* was released from the cantilever surface by flushing with a pH=2.5 glycine/HCl solution.

Figure 5:
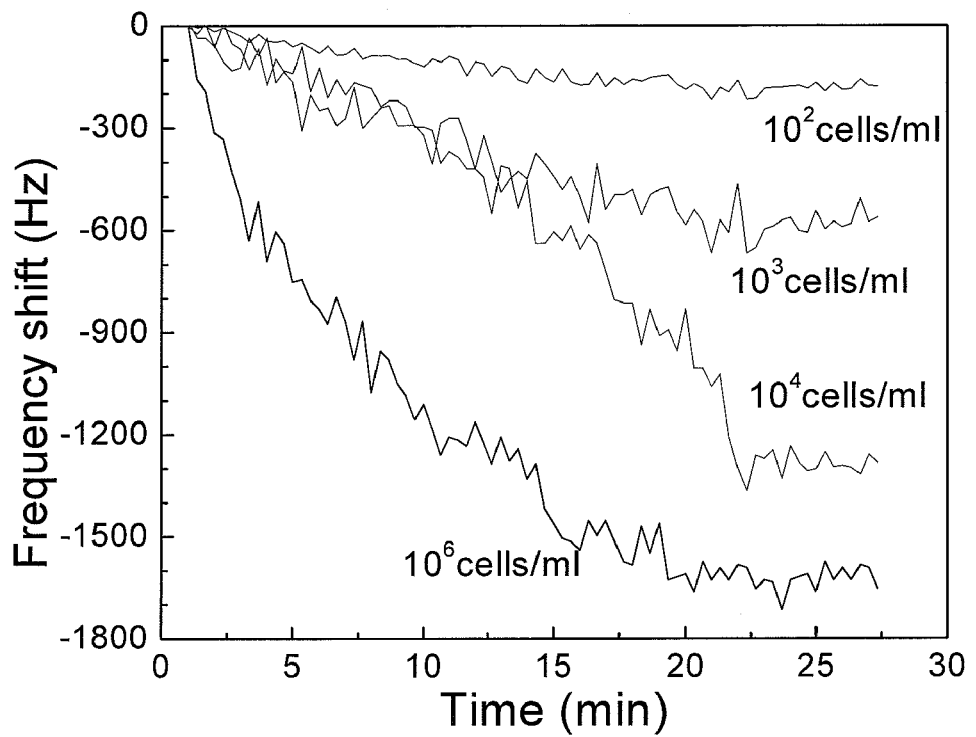
FIG. 5 shows the frequency shift versus time at various E. coli concentrations used in Example 1 under the conditions of flow using the MTMS-insulated PMN-PT/Sn PEMS.

In FIG. 5, the resonance frequency shift versus time obtained with *E. coli* suspensions of various concentrations is plotted. As can be seen, at 10$^6$, 10$^4$, 10$^3$, 10$^2$ cells/ml, resonance frequency shifts of 1600, 1300, 600, and 200 Hz at t=30 min, respectively, were observed. Clearly, all resonance frequency shifts were well above the standard deviation of 75 Hz and the larger resonance frequency shift correlated with a higher concentration.

EXAMPLE 2

Insulation of a Gold Electrode

Similar MTMS insulation layers can be achieved on a noble metal surface by depositing a layer of MPS followed by two coats of MTMS. This insulation method was demonstrated with a PMN-PT/Sn PEMS with a gold electrode on the other side (hereinafter "PMN-PT/Sn/Au"). The PMN-PT/Sn PEMS was first soaked in an 40 mM MPS solution in ethanol, followed by cross-linking in a 0.05 M solution of NaOH (pH=12) and vacuum drying at 35° C. overnight.

Figure 6:
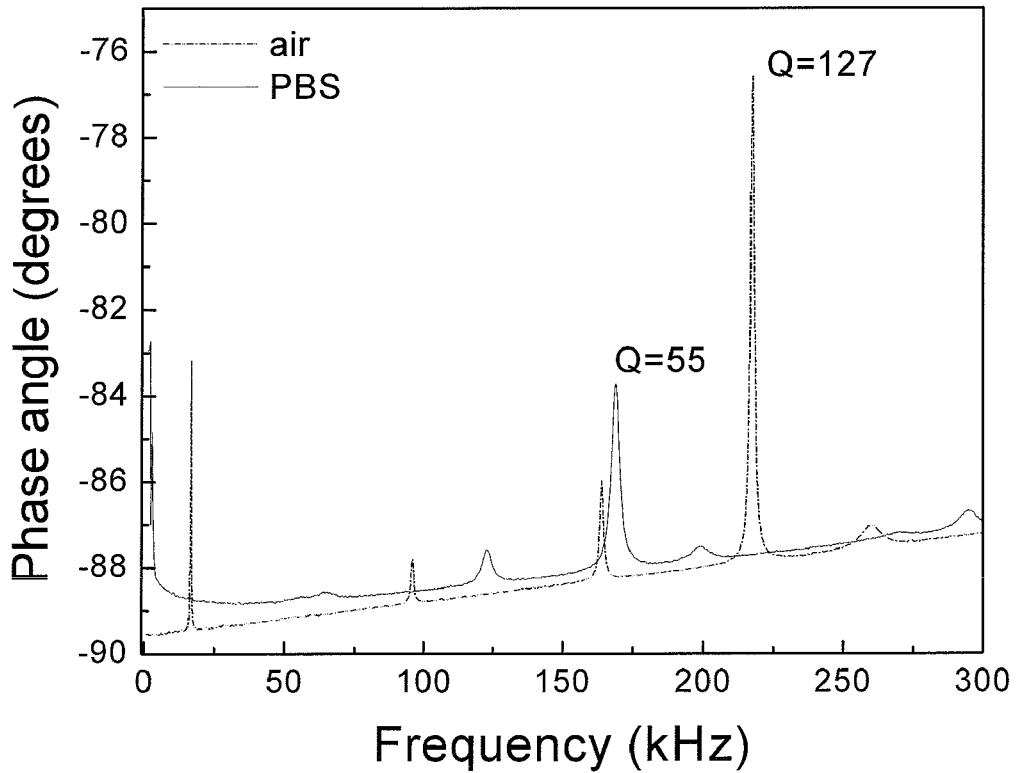
FIG. 6 shows the resonance frequency spectrum of the MTMS-insulated PMN-PT/Sn/Au PEMS of Example 2 with pre-MTMS MPS treatment in air (dashed line) and in a phosphate buffer saline solution (PBS) (solid line).

Two coats of MTMS were then applied using the procedures described above in Example 1 except that cross-linking of the MTMS was carried out at pH-12 for 2 hours rather than at pH=7 overnight. The resonance spectra of the MTMS-insulated PMN-PT/Sn/Au PEMS in air and in PBS are shown in FIG. 6. As can be seen, the in-PBS resonance peak was sharp, retaining a Q value of 55.

Figure 7:
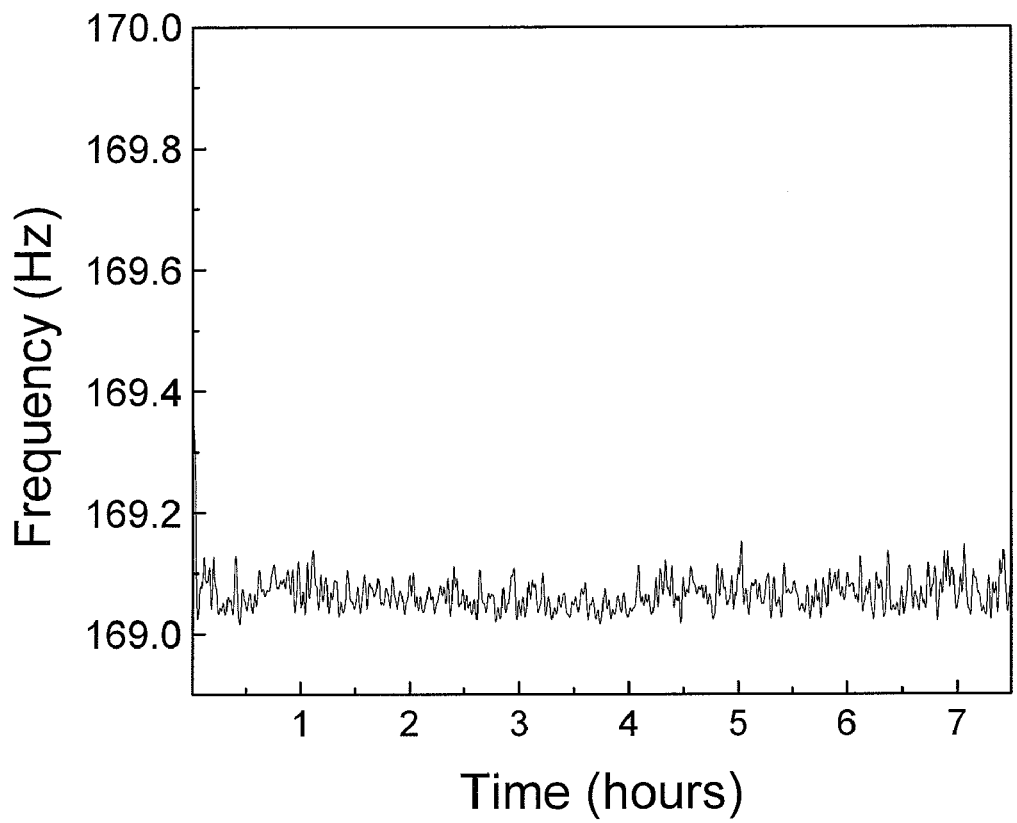
FIG. 7 shows the resonance frequency versus time of the MTMS-insulated PMN-PT/Sn/Au PEMS in a phosphate buffer saline solution (PBS).

In FIG. 7, the resonance frequency versus time of the MTMS-insulated PMN-PT/Sn/Au PEMS in PBS is plotted. As can be seen, the resonance frequency of the MTMS-insulated PMN-PT/Sn/Au PEMS was stable in PBS over 8 hours with a standard deviation no more than 20 Hz. This indicates that the thin MTMS coating layer with a MPS bonding layer can indeed provide the necessary electrical insulation of both the gold and tin surfaces of the PEMS for in-water detection applications.

EXAMPLE 3

Antibody Immobilization on MTMS Insulation Layer

Antibody immobilization on the MTMS surface was realized by coating the MTMS surface with a layer of MPS. The MPS layer was applied in a solution of 1% 3-mercaptopropyl trimethoxysilane, 95% ethanol, and 16 mM acetic acid (pH 4.5). The cantilever was then dried under vacuum overnight at 35° C. (S. L. Beaucage, "Strategies in the Preparation of DNA Oligonucleotide Arrays for Diagnostic Applications," *Current Medicinal Chemistry*, 8, 1213-1244 (2001)). One fourth of the MPS surface was occupied by thiol groups which can be used for covalently immobilizing the receptors via a bi-functional linker, such as sulfosuccinimidyl 4-(N-maleimi-domethyecyclohexane-1-carboxylate (Sulfo-SMCC). The maleimide group of the bi-functional link covalently links the thiol group on the MTMS and the sulfo-NHS ester allows covalent bonding to the primary amine in the antibody.

Figure 8:
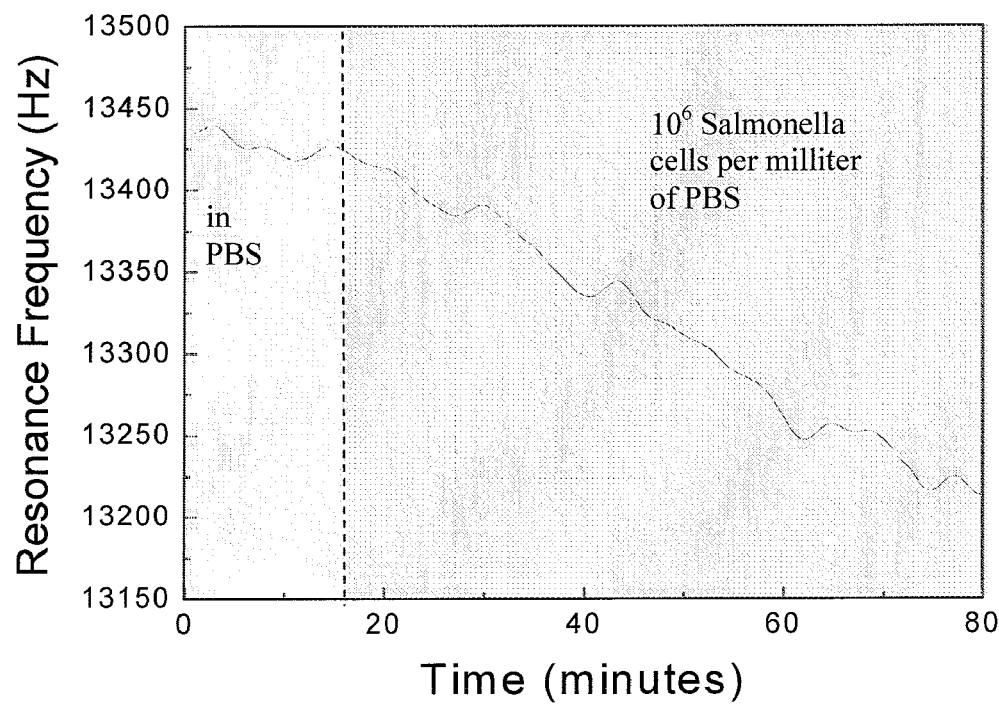
FIG. 8 shows the resonance frequency versus time of the PZT/glass cantilever with the CSA antibody immobilized on the glass tip of the cantilever using the immobilization method described in Example 3, with the MPS as the bi-functional linker.

FIG. 8 shows the detection of *Salmonella* t. at $10^6$ cells/ml using a PZT/glass cantilever with a glass tip. The glass tip was coated with MPS and further immobilized with the anti-CSA antibody. As can be seen, in the first 18 min in PBS, the resonance frequency of the cantilever was stable. Upon immersion of the glass tip of the PZT/glass cantilever in the *Salmonella* t. suspension at t=18 min, the resonance frequency shifted downwardly, indicating that the immobilization on the MTMS was effective and that the sensor can be used to detect *Salmonella* t.

EXAMPLE 4

Insulation and Peptide Conjugation Using MPS 3-mercaptopropyl-trimethoxysilane (MPS) can be used as both an insulating layer and a surface providing a functional group for the covalent immobilization of organic molecules. This example demonstrates the ability to insulate both the PZT/glass and PMN-PT/metal cantilevers with MPS in buffered solutions, and covalently attach synthetic peptides to the surface using a commercially available hetero-bifunctional crosslinker.

A lead zirconate titanate (PZT)/glass PEMS consisted of a PZT layer (T105-H4E-602, Piezo System, Cambridge, Mass.) 127 μm thick, 0.7 mm long, 1.4 mm wide bonded to a 150 μM thick glass layer (Fisher Scientific, Pittsburgh, Pa.) using a nonconductive epoxy (Loctite, Rocky Hill, Conn.) with a 2.2 mm long glass tip. The PZT/glass PEMS is hereinafter referred to as PEMS-A.

In this example, the metal in the PMN-PT cantilever was tin. However, other metals such as nickel, copper and titanium have been successfully insulated in this manner. The PMN-PT/Sn PEMS was 560 μm long and 720 μm wide, consisting of an 8 μm thick PMN-PT layer bonded to a 6 μm thick tin layer, which will be referred to as PEMS-B hereafter. PEMS-B was constructed by first depositing a 30-nm thick nickel layer with a 15-30 nm thick chromium/nickel bonding layer on one side of the PMN-PT freestanding film by evaporation (E-gun Evaporator, Semicore Equipment, Livermore, Calif.) as the electrode. A 4 μm thick tin layer was then electroplated on the nickel surface at a rate of 500 nm/min as the non-piezoelectric layer using a plating solution of tin sulfate titrated with sulfuric acid to a pH=2.5. A 150-nm thick platinum layer was deposited by evaporation onto the other face of the film as the other electrode. Metal electrodes, such as gold, can also serve as electrodes and be insulated with MPS.

The PMN-PT/Sn bilayer was then embedded in wax and cut to the cantilever shape with a wire saw (Princeton Scientific Precision, Princeton, N.J.). After attaching the wires to the top and bottom electrodes using conductive glue (XCE 3104XL, Emerson and Cuming Company, Billerica, Mass.), the PMN-PT/Sn strips were glued to a glass substrate to form the microcantilevers. Optical micrographs of the PZT/glass PEMS (PEMS-A) and of the PMN-PT/PEMS (PEMS-B) are shown in FIGS. 9(*a*) and 9(*b*), respectively.

Prior to thee initial MPS deposition, the PEMS were first cleaned in a diluted (1:100 in water) piranha solution (two parts of 98% sulfuric acid (Fisher, Fair Lawn, N.J.) with one part of 30% hydrogen peroxide (FisherBiotech, Fair Lawn, N.J.)) at 20° C., and rinsed with DI water. For the PZT/glass, the cantilever was soaked in a 1% MPS solution in ethanol titrated to pH=4.5 with acetic acid and covered with paraffin film. Afterwards, the cantilever was rinsed with DI water and dried overnight in a vacuum-oven at 762 mm Hg at 70° C. It was determined that every 2 hours in solution results in a 7 nm thick coating of MPS on the surface. Therefore, the time which the cantilever spent in the solution varied depending upon the desired coating thickness. In this case the total thickness of the coating of MPS on the cantilever surface was 21 nm.

In order to coat the PMN-PT/tin cantilever, the metal electrodes were first coated with MPS using a 40 mM MPS solution in ethanol covered with paraffin film for 4 hours and rinsed by de-ionized (DI) water. The electrodes were then soaked in a 0.01 M NaOH solution overnight for cross-linking, followed by soaking in DI water for 1 hour and overnight vacuum-oven drying (Model 1400E, VWR International) at 762 mm Hg to conclude the first MPS coating.

If the metal was copper instead of tin the procedure was changed to accommodate the copper. PMN-PT/Cu cantilevers were successfully insulated using a 0.1 mM MPS solution in ethanol for 30 minutes followed by rinsing and vacuum drying to provide an initial coating. Following the initial layer of MPS deposition the cantilever was soaked in a 1% MPS solution in ethanol titrated to pH=4.5 with acetic acid and covered with paraffin film. Again, it was determined that every 2 hours spent in this solution produced a 7 nm thick coating of MPS. Shorter soaking times resulted in thinner layers, while longer times can produce thicker layers. In the present case a coating thickness of 21 nm was used.

Figures 9A, 9B:
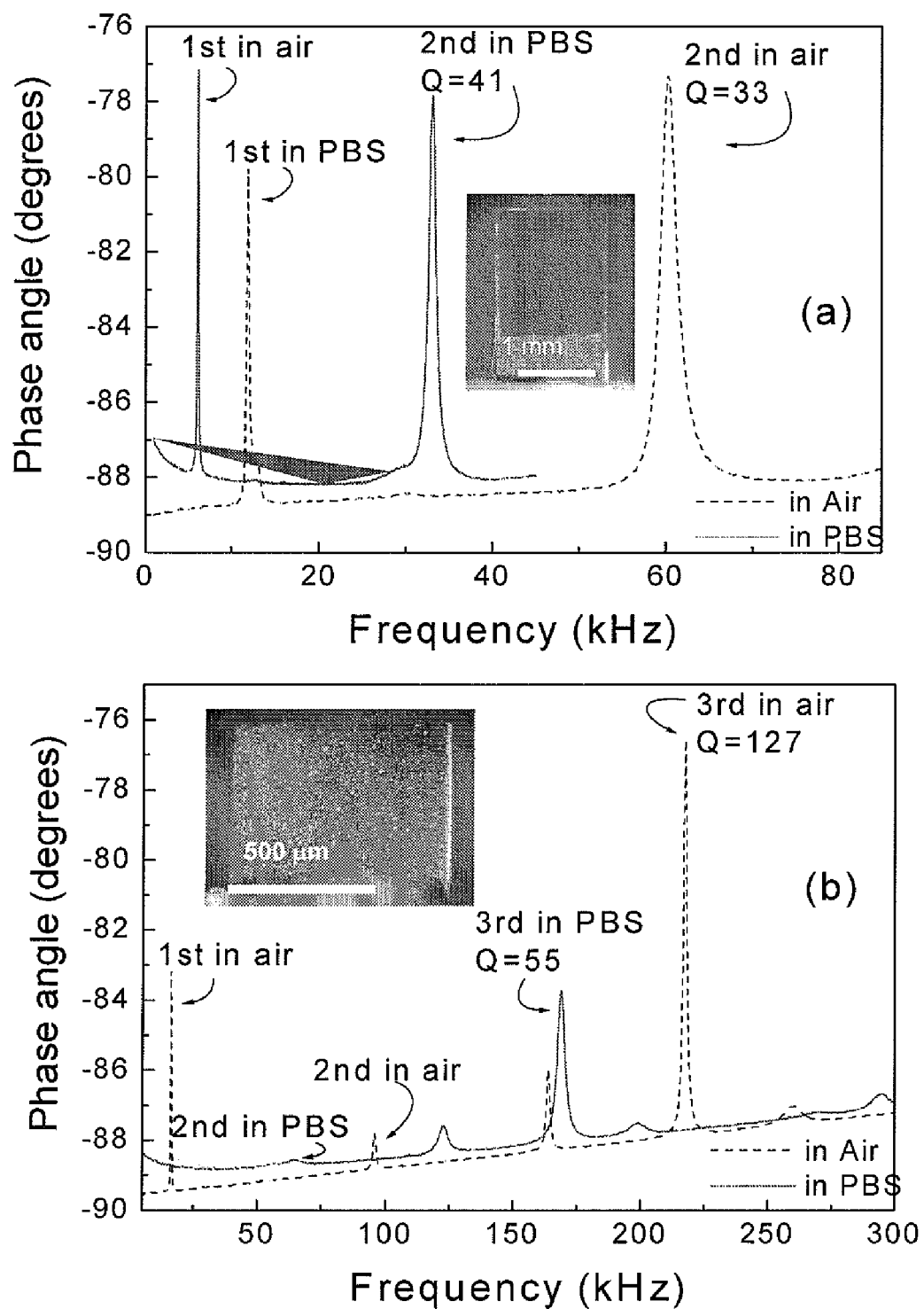
FIG. 9(a) shows phase angle versus frequency resonance spectra of PEMS-A when in air (dashed line), and when submerged in a solution of PBS (solid lines), as well as an optical micrograph of the PZT/glass PEMS (PEMS-A) of Example 4 as an inset.
FIG. 9(b) phase angle versus frequency resonance spectra of PEMS-B when in air (dashed line), and when submerged in a solution of PBS (solid lines), as well as an optical micrograph of the PMN-PT/PEMS (PEMS-B) of Example 4 as an inset.

To examine the electrical insulation properties of the MPS coating, the MPS-coated PEMS were submerged in a phosphate buffered saline (PBS) solution. The resultant resonance spectra of the MPS-coated PEMS-A and those of the MPS-coated PEMS-B are shown in FIGS. 9(a) and 9(b), respectively, as phase angle versus frequency plots, both in air (dashed lines) and in PBS (solid lines). As can be seen from these figures, both PEMS-A and PEMS-B retained two resonance peaks in PBS, the first and the second flexural peaks in the case of PEMS-A and the second and the third flexural peaks in the case of PEMS-B. The reduced resonance peak intensities and resonance frequencies in PBS were respectively due to the viscous damping and the mass of the liquid that moved in phase with the PEMS. For the PEMS-A the Q value was 33 in air and 41 in PBS as shown in FIG. 9 (a), and for PEMS-B, the Q value was 127 in air and 55 in PBS, as shown in FIG. 9(b).

Figure 10:
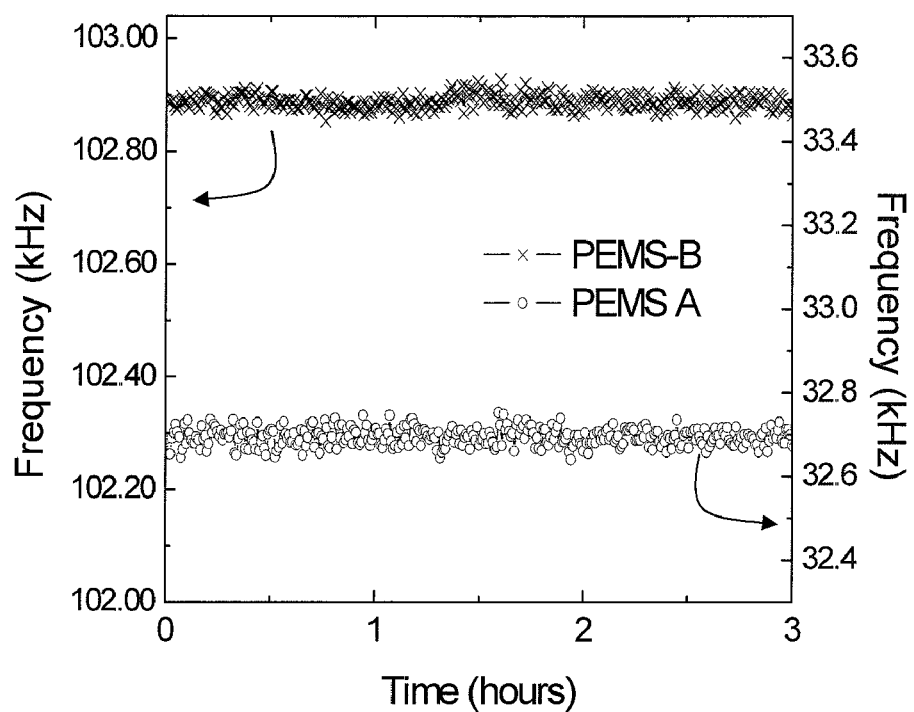
FIG. 10 shows the resonance frequency versus time of PEMS-B (crosses) and PEMS-A (open circles) in PBS obtained in Example 4. The standard deviation of resonance frequency was 21 Hz for PEMS-A and 13 Hz for PEMS-B.

To assess how stable the spectra were in PBS, the resonance peak frequencies of MPS-coated PEMS in PBS were monitored for 3 hours. As an example, FIG. 10 shows the resonance frequency of PEMS-B versus time over the 3-hour period. As can be seen from FIG. 10, the resonance frequency of PEMS-B remained stable with a standard deviation of about 14 Hz throughout the 3-hour period, indicating that the resonance frequency of the PEMS could indeed be used as indicator to monitor detection in PBS.

In order to demonstrate covalent conjugation to the MPS surface, sulfosuccinimidyl-4-(N-maleimidomethyl)cyclohexane-1-carboxylate (sulfo-SMCC) (Pierce) was used as the bi-functional linker to crosslink the primary amine in a synthetic peptide (single chain variable fragment) to the sulfhydryl group of MPS. First, the scFv was linked to sulfo-SMCC by mixing 500 µl of 600 nM scFv solution with 1 ml of 5 mM sulfo-SMCC solution for 1 hour for the NHS-ester in the sulfo-SMCC to react with a primary amine of the scFv. Unreacted sulfo-SMCC molecules were then removed by microcentrifugation at 4000 RPM with a 10 kD filter (Millipore) repeated four times. The MPS-coated PEMS was then soaked in the sulfo-SMCC-linked scFv solution for 1 hour to immobilize the scFv on the MPS coating surface via the reaction of the maleimide of the sulfo-SMCC with the sulfhydryl of the MPS.

Figure 11:
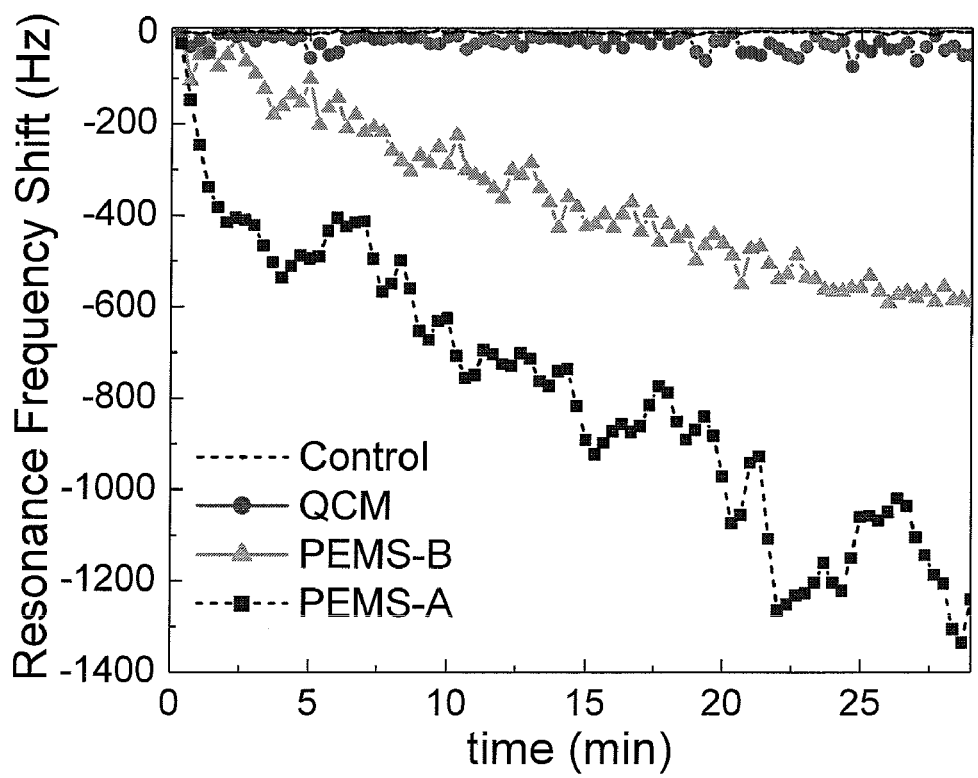
FIG. 11 shows the resonance frequency shift versus time for scFv immobilization as in Example 4 using PEMS-A (squares), PEMS-B (triangles), QCM (circles) and a control (PBS on QCM) (dashed line).

To measure the quantity of protein on MPS coating, the scFv immobilization procedure was carried out on a MPS-coated 5 MHz QCM and a resonance frequency shift, $\Delta f_{QCM}$=-40 Hz was obtained, which is shown along with the resonant frequency shift recorded for PEMS-A, PEMS-B, and a control (PBS on MPS-coated QCM) in FIG. 11. The adsorption density, $\Gamma$, of the SMCC-linked scFv on the MPS-coated QCM can be estimated using Sauerbrey equation: $\Delta f_{QCM}$=[$2f^2_{QCM}/\sqrt{(G\rho)}$]. With $f_{QCM}$=5 MHz, and $\Delta f_{QCM}$= -40 Hz at 30 minutes as can be seen from FIG. 11, the Sauerbrey equation gave $\Gamma$=7×10$^{-6}$ kg/m$^2$. The mass detection sensitivity of the cantilever $(\Delta m/\Delta f)cant$ can be calculated using the equation $(\Delta m/\Delta f)_{cant}$=$\Gamma A_{cant}/\Delta f_{cant}$, where $\Delta f_{cant}$ and $A_{cant}$ were the resonance frequency shift and the areas of the cantilever. Given that the surface area of PEMS-A and that of PEMS-B were 8×10$^{-6}$ and 7×10$^{-7}$ m$^2$, respectively, the total masses of the adsorbed SMCC-linked scFv on PEMS-A and PEMS-B were 5.6×10$^{-8}$ and 5.0×10$^{-9}$ g, respectively.

EXAMPLE 5

Thicker Insulation Layers

Layers of up to 300 nm in thickness can be deposited using the same procedure outlined in Example 4. These insulation layers have been shown to be successful at insulating the cantilever and capable of covalent immobilization. In order to demonstrate this, a 300 nm thick coating of MPS was deposited on a PZT/glass cantilever using the methods described above. A protein was then immobilized to the MPS layer. The protein used for this study was an engineered antibody fragment, known as single chain variable fragment (scFv) synthesized by Greg Adams at the Fox Chase Cancer Center specific to Her2. Her2 is an epidermal growth factor receptor whose high concentrations have been linked to breast cancer.

Subsequently, the unreacted sites were blocked with bovine serum albumin (BSA), and then the cantilever was used for detection of a protein (Her2) in diluted serum (1:40; Serum:PBS).

Figure 12:
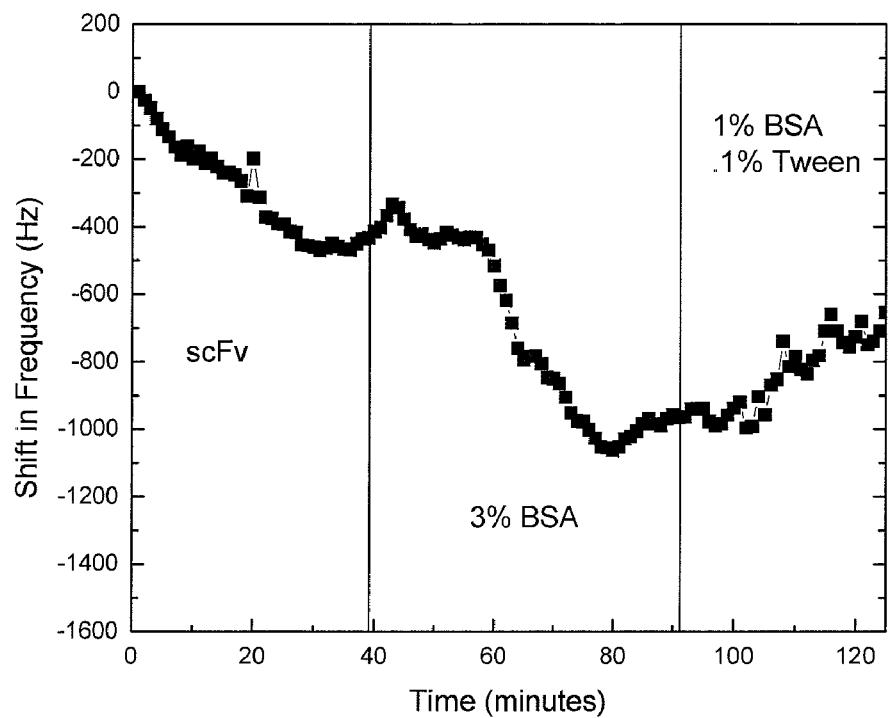
FIG. 12 shows the resonance frequency shift versus time for scFv immobilization, followed by 3% BSA blocking and a 1% BSA & 0.1% Tween-20TH rinse of Example 5.

Immobilization of a single chain variable fragment was performed using the same procedure outlined in Example 4 for sulf-SMCC conjugation. The cantilever was then rinsed with PBS and soaked in a 3% BSA for 50 minutes. Finally, the cantilever was rinsed with a 1% BSA & 0.1% Tween-20TH solution for 30 minutes. The response of the cantilever during this immobilization procedure is shown in FIG. 12. The figure shows a 450 Hz down-shift for the scFv, a 625 Hz down-shift for the 3% BSA and a 320 Hz up-shift during the 1% BSA & 0.1% Tween-20TH rinse.

Figure 13:
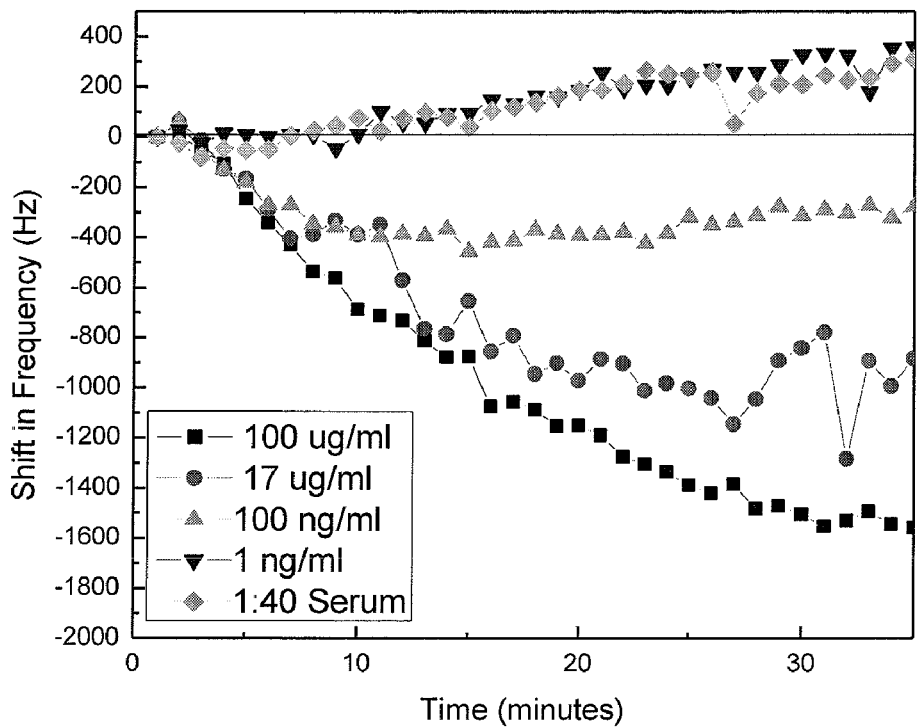
FIG. 13 shows the resonance frequency shift versus time for detection of Her2 in diluted serum for various concentrations of Her2 as in Example 5.

After immobilization, the cantilever was used for five 35-minute experiments to detect a protein (Her2) in a background of diluted serum (1:40). FIG. 13 depicts the results of these experiments. The figure shows that when Her2 was present in concentrations detectable by the cantilever there was a shift in the resonance frequency. The shift was -1580 Hz for 100 µg/ml, -900 Hz for 17 µg/ml and -325 Hz for 100 ng/ml. However when Her2 was present in concentrations too low to be detected, the change in resonant frequency was identical to the control (1:40 serum). After each trial the cantilever was soaked in a 0.1 M solution of glycine titrated to a pH of 2.5 using HCl for 10 minutes in order to release the Her2 bound by the scFv. After treatment with the glycine wash, the cantilever was rinsed with PBS for 3 minutes.

Figure 14:
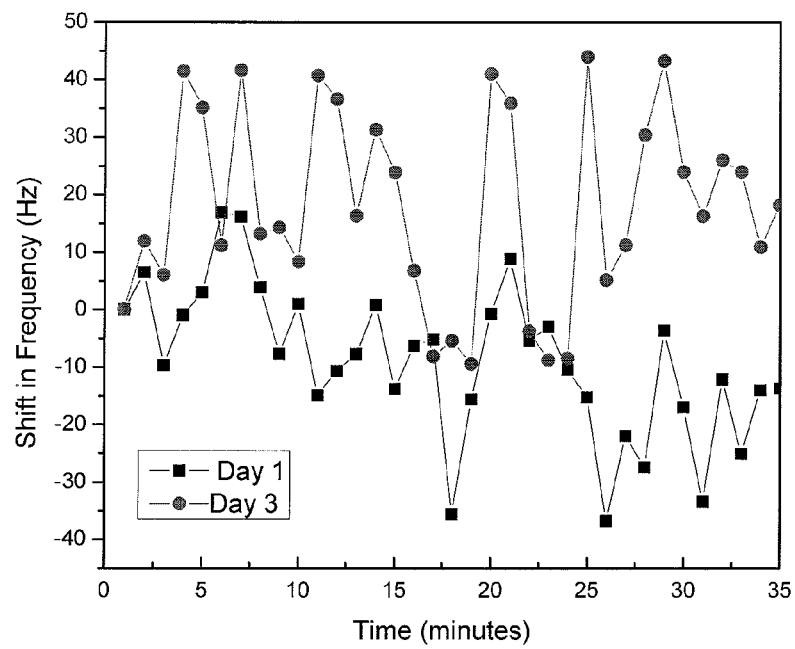
FIG. 14 shows a comparison of the background resonance frequency shift of the MPS coated cantilever in PBS solution between the first day and final day of experimentation in Example 5. The peak is quite stable with a standard deviation of 13 for day 1 and 17 for day 3.

The above experiments were conducted over the period of 3 days. At the end of 3 days the cantilever was still functional and stable in PBS solution; however the scFv had been degraded by the glycine solution. Each day the cantilever was soaked in PBS media, diluted serum, or the release buffer for a period of 7 hours. After each 7 hour experiment the cantilever was rinsed with PBS, and then placed in a humidified chamber at 4° C. The stabilities of the cantilever in PBS on the first and final days are compared in FIG. 14. The peak was quite stable with a standard deviation of 13 for day 1 and 17 for day 3.

Figure 15:
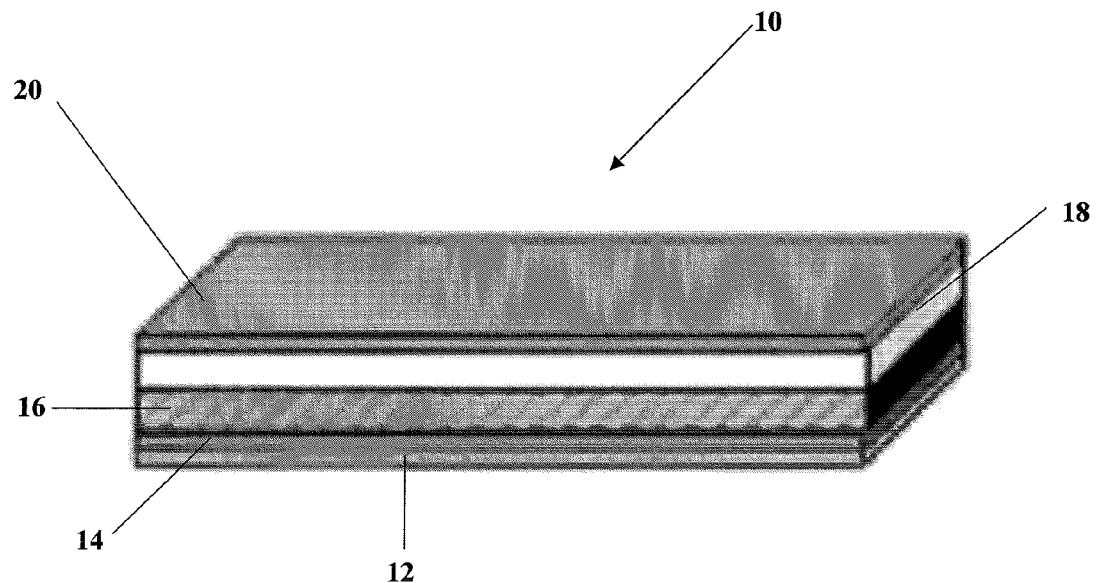
FIG. 15 is a schematic diagram showing a cross section of a piezoelectric microcantilever sensor (PEMS) in accordance with one embodiment of the present invention.

FIG. 15 shows a schematic representation of a cross-section of one embodiment of a piezoelectric microcantilever sensor 10 in accordance with the present invention. This embodiment includes an antibody layer 12, a platinum layer 14, a PMN-Pt layer 16, a tin layer 18 and an MTMS insulation layer 20.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A device comprising:
    a substrate comprising a metal or a metal with a metal oxide surface,
    an insulation layer derived from bi-functional molecules, said bi-functional molecules comprising a hydrophobic group and a group covalently bound to the metal or metal oxide surface of the substrate, wherein the insulation layer has a thickness of 1-10 nm and wherein the bi-functional molecules comprise methyltrimethoxysilane, and
    at least a second bi-functional molecule having the structure (I):

$$(RO)_3Si(CH_2)_y-X \qquad (I)$$

wherein y is an integer from 1-20, each RO— represents a hydrolysable silanol group bonded to the silicon atom, and X represents a hydrophobic organo-functional group other than a methyl group.

2. A device as claimed in claim 1, wherein the hydrophobic group is selected from the group consisting of alkyl, phenyl, alkyl halide, alkene, alkyne, and sulfhydryl.

3. A device as claimed in claim 2, wherein said at least one second bi-functional molecules is bound to the substrate by a silanol group.

4. A device as claimed in claim 1, further comprising proteins, small peptide chains or DNA coupled to a surface of the insulation layer.

5. A device as claimed in claim 4, wherein the proteins, small peptide chains or DNA are covalently bound to the surface of the insulation layer.

6. A device comprising:
    a substrate comprising a metal or a metal with a metal oxide surface,
    an insulation layer derived from bi-functional molecules, said bi-functional molecules comprising a hydrophobic group and a group covalently bound to the metal or metal oxide surface of the substrate, wherein the insulation layer has a thickness of 1-10 nm and wherein the bi-functional molecules comprise methyltrimethoxysilane, and
    proteins, small peptide chains or DNA coupled to a surface of the insulation layer.

7. A device as claimed in claim 6, wherein the proteins, small peptide chains or DNA are covalently bound to the surface of the insulation layer.

8. A device comprising:
    a substrate comprising a metal or a metal with a metal oxide surface,
    an insulation layer derived from bi-functional molecules, said bi-functional molecules comprising a hydrophobic group and a group covalently bound to the metal or metal oxide surface of the substrate, wherein the insulation layer has a thickness of 1-10 nm and wherein the bi-functional molecules comprise methyltrimethoxysilane, and
    wherein the device further comprises 3-mercaptopropyl-trimethoxysilane as a second bi-functional molecule.

9. A device as claimed in claim 8, further comprising proteins, small peptide chains or DNA coupled to a surface of the insulation layer.

10. A device as claimed in claim 9, wherein the proteins, small peptide chains or DNA are covalently bound to the surface of the insulation layer.

11. An insulated piezoelectric cantilever suitable for use in an aqueous environment comprising:
    a piezoelectric layer,
    at least one conductive layer in contact with the piezoelectric layer, said at least one conductive layer comprising a metal or a metal with a metal oxide surface, and
    an insulation layer including a reactive silanol group, said insulation layer being derived from bi-functional molecules, said bi-functional molecules comprising a hydrophobic group and
    said bi-functional molecules being covalently bound directly to a surface of one said conductive layer by a silanol group or when said surface of the conductive layer comprises gold, platinum or copper, said bi-functional molecules being covalently bound directly to the surface of one said conductive layer by a sulfhydryl group.

12. An insulated piezoelectric cantilever as claimed in claim 11, wherein the hydrophobic group is selected from the group consisting of alkyl, phenyl, alkyl halide, alkene, alkyne, and sulfhydryl.

13. An insulated piezoelectric cantilever as claimed in claim 11, wherein the bi-functional molecules comprise methyltrimethoxysilane.

14. An insulated piezoelectric cantilever as claimed in claim 11, wherein the bi-functional molecules comprise 3-mercaptopropyl-trimethoxysilane.

15. An insulated piezoelectric cantilever as claimed in claim 11, further comprising proteins, small peptide chains or DNA coupled to a surface of the insulation layer.

16. An insulated piezoelectric cantilever as claimed in claim 15, wherein the proteins, small peptide chains or DNA are covalently bound to the surface of the insulation layer.

17. An insulated piezoelectric cantilever as claimed in claim 15, wherein the bi-functional molecules comprise a group selected from the group consisting of hydroxyl, thiol, amine, amide, carboxylic acid, aldehyde, ketone anhydride halide, alkene, alkyne, which couples the proteins, small peptide chains or DNA to a surface of the insulation layer.

18. An insulated piezoelectric cantilever as claimed in claim 11, wherein the insulation layer has a thickness of 1 to 2000 nm.

19. An insulated piezoelectric cantilever as claimed in claim 11, wherein the insulation layer has a thickness of 1 to 10 nm.

* * * * *